United States Patent [19]
Martin et al.

[11] Patent Number: 5,506,364
[45] Date of Patent: * Apr. 9, 1996

[54] PROCESS FOR THE PRODUCTION OF BIS(FLUOROMETHYL)ETHER AND DIFLUOROMETHANE

[75] Inventors: John S. Martin, Northwich; Thomas A. Ryan, Kelsall, both of England; Rachel A. Spooncer, Manley, Great Britain

[73] Assignee: Imperial Chemical Industries PLC, London, England

[*] Notice: The portion of the term of this patent subsequent to Sep. 6, 2011, has been disclaimed.

[21] Appl. No.: 238,448

[22] Filed: May 5, 1994

Related U.S. Application Data

[63] Continuation of Ser. No. 145,668, Nov. 4, 1993, Pat. No. 5,344,998, which is a continuation of Ser. No. 974,710, Nov. 12, 1992, abandoned.

[30] Foreign Application Priority Data

Nov. 13, 1991 [GB] United Kingdom .................. 9124087

[51] Int. Cl.$^6$ .................................................. C07C 41/00
[52] U.S. Cl. ................................................ 568/687; 570/142
[58] Field of Search ............................... 568/687; 570/142

[56] References Cited

U.S. PATENT DOCUMENTS

| | | | |
|---|---|---|---|
| 3,377,394 | 4/1968 | Boudakian et al. | 570/142 |
| 4,143,078 | 3/1979 | Gibbs et al. | 570/142 |
| 5,073,236 | 12/1991 | Gelbein et al. | 203/29 |

FOREIGN PATENT DOCUMENTS

| | | |
|---|---|---|
| 1025856 | 3/1958 | Germany . |
| 2126216 | 3/1984 | United Kingdom . |

OTHER PUBLICATIONS

Weinmayr, Hydrogen Fluoride as a Condensing Agent. VI. REactions of Fluoroolefins with Formaldehyde in . . . , The Journal of Organic Chemistry, vol. 28, No. 2, Feb., 1963, pp. 492–494.

West German Published Patent Application 1 025 856, Production of bis–methyl chloride ether, 1985.

Primary Examiner—Gary L. Geist
Assistant Examiner—Catherine S. Kilby Scalzo
Attorney, Agent, or Firm—Cushman Darby & Cushman

[57] ABSTRACT

A process for the production of bis(fluoromethyl)ether by contacting formaldehyde with hydrogen fluoride in a reaction/distillation vessel. The reaction/distillation vessel is preferably a reaction/distillation column through which formaldehyde and hydrogen fluoride preferably flow in counter current.

The bis(fluoromethyl)ether may be converted to difluoromethane, preferably by heating the bis(fluoromethyl)ether to elevated temperature in the presence of a metal, metal oxide, metal fluoride or metal oxyfluoride catalyst.

12 Claims, 4 Drawing Sheets

PROCESS FOR THE PRODUCTION OF BIS(FLUOROMETHYL)ETHER AND DIFLUOROMETHANE

This is a continuation of U.S. application Ser. No. 08/145,668, filed Nov. 4, 1993, now U.S. Pat. No. 5,344,998, which is a continuation of U.S. application Ser. No. 07/974,710, filed Nov. 12, 1992, now abandoned.

This invention relates to a chemical process, in particular a process for the production of bis(fluoromethyl)ether by the reaction of formaldehyde with hydrogen fluoride and to a process for the production of difluoromethane incorporating the step of producing bis(fluoromethyl)ether from formaldehyde and hydrogen fluoride.

Formaldehyde and hydrogen fluoride react together to produce bis(fluoromethyl)ether and water. The reaction is equilibrium limited, there being only about a 55% conversion of formaldehyde to bis(fluoromethyl)ether at 20° C. even using a 7:1 molar excess of hydrogen fluoride to formaldehyde to drive the equilibrium towards the products. We have discovered that in order to overcome this equilibrium problem, one or both of the products may be removed from the reaction mixture as soon as possible after it/they are formed in order to drive the equilibrium towards the products and achieve higher conversions of formaldehyde to bis(fluoromethyl)ether.

Furthermore, bis(fluoromethyl)ether is useful as a starting material for the production of difluoromethane and methyl fluoride by heating bis(fluoromethyl)ether to elevated temperature in the presence of a suitable catalyst and it is desirable that water is not present significant amounts in the the bis(fluoromethyl)ether which is heated since we have found that water promotes undesirable side reactions, and promotes decomposition of bis(fluoromethyl)ether to formaldehyde and hydrogen fluoride. Thus it is desirable for water to be removed from the water and bis(fluoromethyl)ether reaction product mixture before the bis(fluoromethyl)ether is further treated to produce difluoromethane.

We have now found that the aforementioned separation of products from reactants and also separation of water from bis(fluoromethyl)ether may be achieved efficiently using reactive distillation.

According to the present invention there is provided a process for the production of bis(fluoromethyl)ether which comprises contacting formaldehyde with hydrogen fluoride in a reaction/distillation vessel. By a reaction/distillation vessel, there is meant a vessel in which hydrogen fluoride and formaldehyde are contacted in order to produce bis(fluoromethyl)ether, and from which the vapour in the vessel is separated from the liquid in the vessel and withdrawn. In terms of the products of the reaction (equimolar amounts of bis(fluoromethyl)ether and water), the vapour is rich in bis(fluoromethyl)ether relative to water, i.e. the molar ratio of bis(fluoromethyl)ether to water is greater than 1, whilst the liquid is rich in water relative to bis(fluoromethyl)ether.

The vessel may comprise a pot or flask constructed from suitable materials having resistance to the hydrogen fluoride/formaldehyde and product mixtures, in which a batch process is operated, that is in which a single stage distillation is effected. In this case, formaldehyde and hydrogen fluoride may be charged to the pot and the pot may be heated in order to drive the vapours from the pot thereby separating the vapours from the liquid. If desired the vapours may then be condensed and charged to a further vessel in which a further single distillation separation is effected. This procedure may be repeated in a series of vessels in which in each of which a batch distillation is effected.

Preferably however the process of the invention is conducted in a continuous manner in which the reaction/distillation vessel comprises a reaction/distillation column having a plurality of reaction/distillation stages.

According to a preferred embodiment of the invention there is provided a process for the production of bis(fluoromethyl)ether which comprises contacting formaldehyde with hydrogen fluoride in a reaction/distillation column.

In the process of this preferred embodiment of the invention, formaldehyde and hydrogen fluoride may be fed continuously to the reaction/distillation column (hereinafter simply referred to as "the column") and bis(fluoromethyl)ether and hydrogen fluoride in high purity, for example as pure as 99.5% hydrogen fluoride and bis(fluoromethyl)ether, may be continuously withdrawn from the top of the column whilst water and water/hydrogen fluoride azeotrope, also formed during the process, may be removed from the bottom of the column. In this process, the removal of hydrogen fluoride and bis(fluoromethyl)ether at each reactive distillation stage within the column increases the extent of reaction achieved at each stage within the column, thus providing very high, indeed substantially complete, conversions of formaldehyde to bis(fluoromethyl)ether.

The column in which the process is carried out may be a conventional distillation column, in which may be provided, for example, bubble cap trays or sieve plates with associated wiers and downcomers. The column may be a packed column which may be provided with random or structured packing.

The column, or at least the internal surfaces of the column and other components, in particular the internal components within the column, for example the packing, sieve plates or bubble cap trays which are in contact with the reactant/product mixture, should be constructed from materials which are resistant to the corrosive combination of hydrogen fluoride and water. Thus, the column and associated apparatus may be constructed from, for example, a Hastelloy or Inconel alloy, or from a polyfluorinated polymer, for example polytetrafluoroethylene, or "FEP", a copolymer of tetrafluoroethylene and perfluoropropylene. The column may be made completely from such a material or the column may be constructed from, for example, steel which is coated or lined with a material resistant to the corrosive combination of hydrogen fluoride and water.

In carrying out the preferred embodiment of the process of the invention, the column effectively comprises three functional sections, a central "reaction" section in which hydrogen fluoride and formaldehyde contact each other, an upper "bis(fluoromethyl)ether/hydrogen fluoride" rectifying section in which bis(fluoromethyl)ether and hydrogen fluoride are separated from heavier components present and a lower stripping section in which water and the water/hydrogen fluoride azeotrope are separated from lighter components.

The water/hydrogen fluoride azeotrope recovered from the column may then be contacted with sulphuric acid in order to recover hydrogen fluoride which may be recycled to the column. Alternatively a further stripping section may be provided at the bottom of the column to which sulphuric acid is fed in order to recover hydrogen fluoride from the hydrogen fluoride/water azeotrope within the column.

The size of the column may vary considerably depending upon the desired production rate and the operating reflux and reboil ratios. However, for typical commercial production rates, the number of practical distillation stages within the column will usually be at least 20, that is at least 5 rectifying stages, at least 5 stripping stages and at least 10 reaction stages.

There is no limit to the number of stages which may be provided within the column although there is generally no need for there to be in excess of 150 stages. Preferably the column comprises from about 30 to about 50 practical stages.

Where a packing is employed within the column, a practical stage is measured in terms of the "height of packing equivalent to a theoretical distillation plate" or "HETP"; that is the height of packing which performs the same degree of separation as a theoretical distillation plate.

The HETP depends upon the particular packing employed in the column but will typically be in the range from about 0.1 meter to about 1 meter. Thus the column will typically comprise from about 20 meters to about 35 meters of packing in total.

Where sieve plates or bubble cap trays are employed in the column, two sieve plates or bubble cap trays correspond to about one practical distillation stage.

We generally prefer that the packing, sieve plates or bubble cap trays required for each functional section in the column are separate from the packing, plates or trays required for the other functional sections, although the functional sections may simply be zones within a continuous packing or stack of plates/trays within the column. Thus, for example, reactant feed distributors may conveniently be positioned between the packing, plates or trays within the column which correspond to different functional sections.

The formaldehyde may be fed to the column in any of its known forms although we generally prefer to feed formaldehyde in the liquid or vapour phase. Thus the formaldehyde may be provided, for example, in one of its polymeric forms, paraformaldehyde or trioxane which may be in the form of an aqueous solution, generally known as formalin, or in its monomeric form, which may be provided for example, from a process stream in which it has been freshly prepared, for example by the oxidation of methanol. Accordingly, whenever used herein, the term "formaldehyde" is to be understood as including formaldehyde in any of its known forms.

We prefer to introduce formaldehyde into the column in the form of a solution of formaldehyde in hydrogen fluoride, since this reduces the water content within the column. In this case, some reaction may take place in the feed stream so that the feed stream will also contain some bis(fluoromethyl)ether and water. However, the presence of bis(fluoromethyl)ether and water in the feed stream does not effect the operation of the process significantly and substantially complete conversions of formaldehyde and high purity of products are still achieved.

The formaldehyde and hydrogen fluoride may be fed to the column through the same inlet, that is they may be fed to the same position within the column. Preferably however, at least some of the hydrogen fluoride and the formaldehyde are fed through different inlets, the formaldehyde being introduced into the column at a position above that at which hydrogen fluoride is introduced into the column, the formaldehyde and hydrogen fluoride then flowing counter-current to each other through the column as a natural consequence of their different boiling points. Thus where formaldehyde is introduced into the column as a solution in liquid hydrogen fluoride, some hydrogen fluoride is introduced to the column through the formaldehyde inlet but an additional and separate feed of hydrogen fluoride is preferred at a position in the column below that at which the formaldehyde is introduced. We especially prefer that the formaldehyde is introduced into the column at the position between the rectifying and reaction sections of the column and that hydrogen fluoride is introduced at a position between the reaction and stripping sections of the column. The hydrogen fluoride which is introduced into the column through the hydrogen fluoride inlet may be introduced as a liquid or as a vapour although we prefer, in order to reduce the heat duty applied to the column, to introduce hydrogen fluoride vapour.

The molar proportions of total hydrogen fluoride and formaldehyde which are introduced into the column may vary considerably, for example in the range from about 0.5:1 to about 50:1 but in general a stoichiometric excess of hydrogen fluoride is preferred. Typically the molar ratio of hydrogen fluoride to formaldehyde will be in the range from about 2:1 to about 10:1.

The relative flow rates of formaldehyde and hydrogen fluoride into the column will be such as to produce the desired proportion of hydrogen fluoride and formaldehyde within the column and the absolute flow rates will also be such as to give the desired production rate and product composition at the particular operating reflux ratio. The reflux ratio is defined as the ratio of product stream recycled back into the column to product stream collected. The reflux ratio will typically be at least 0.1 and is preferably within the range 0.3 to 10. Thus, for example, for a production rate of 20,000 tonnes per year of bis(fluoromethyl)ether using a 37% formalin solution as formaldehyde feed and a 10:1 molar excess of hydrogen fluoride with a reflux ratio of 5, the flow rates of formalin and hydrogen fluoride into the column will be about 5,000 (equivalent to 1,825 of formaldehyde per hour) and about 12,000 kg per hour respectively.

The column is typically operated at a temperature in the reaction section in the range from about 50° C. to about 80° C. However, the particular temperature is dependent upon a number of factors including for example, the reactant flow rates, the operating pressure and desired production rate. The temperature profile within the whole of the column will typically be from about 20° C. to about 40° C. at the top of the column to from about 115° C. to about 140° C. at the bottom of the column.

Heat may be supplied to the process by any conventional means, for example sparging steam into the base heater or by the use of a reboiler.

The column may typically be operated at about ambient pressure although superatmospheric or subatmospheric pressures may be used if desired. We have found that where superatmospheric pressures and therefore higher temperatures are employed, there is an increased tendency for monofluoromethane to be produced within the column.

As previously stated, very high purity bis(fluoromethyl)ether and hydrogen fluoride may be withdrawn continuously from the top of the column. This stream may, if desired, be further purified in order to separate the components, i.e. to separate hydrogen fluoride from bis(fluoromethyl)ether and/or in order to separate the main components from minor contaminants which may be present in the stream. This further purification may be carried out using conventional techniques, for example by passage of the product stream through one or more additional distillation columns.

Alternatively and in a further embodiment of the process, a further rectifying section may be provided within the column above the "hydrogen fluoride/bis(fluoromethyl)ether" rectifying section in order to separate hydrogen fluoride from bis(fluoromethyl)ether within the column. In this case, hydrogen fluoride may be recovered from the top of the column and bis(fluoromethyl)ether may be taken from the column as a sidestream at a position between the "hydrogen fluoride/bis(fluoromethyl)ether" rectifying section and the additional rectifying section.

The process of the present invention facilitates production of bis(fluoromethyl)ether and hydrogen fluoride of sufficiently high purity that the bis(fluoromethyl)ether stream may be passed directly, optionally after removing hydrogen fluoride, to a reaction zone in which the bis(fluoromethyl)ether is converted to difluoromethane.

According to a further preferred embodiment of the invention there is provided a process for the production of difluoromethane which comprises (a) contacting formaldehyde with hydrogen fluoride in a reaction/distillation vessel as previously described and (b) feeding the bis(fluoromethyl)ether from step (a) to a reaction zone whereby to produce difluoromethane.

Step (b) of this preferred embodiment of the invention may be effected in the liquid or vapour phase. We prefer that step (b) is effected in the vapour phase by heating the bis(fluoromethyl)ether from step (a) to elevated temperature. Preferably therefore the bis(fluoromethyl)ether from step (a) is fed to a heating zone.

Heating of the bis(fluoromethyl)ether may be carried out in the presence of hydrogen fluoride vapour. The hydrogen fluoride may be that present in the bis(fluoromethyl)ether stream produced in step (a) or additional hydrogen fluoride may be fed to step (b).

Heating of the bis(fluoromethyl)ether in step (b) to produce difluoromethane may advantageously be performed in the presence of a catalyst. The conversion of bis(fluoromethyl)ether and selectivity to difluoromethane are dependent upon the choice of catalyst and we have found that whilst certain catalysts promote a high degree of selectivity to difluoromethane, other catalysts promote a high degree of selectivity to monofluoromethane and still other catalysts yield mixtures of both difluoromethane and monofluoromethane.

The catalyst may be for example a metal, including for example an s-block metal such as calcium, a p-block metal such as aluminium, tin or antimony, an f-block metal such as lanthanum or a d-block metal such as nickel, copper, iron, manganese, cobalt and chromium or alloys thereof; a metal oxide, for example chromia or alumina, a metal fluoride, for example, aluminium, manganese or chromium fluoride, or a metal oxyfluoride, for example an oxyfluoride of one of the aforementioned metals. The metal is preferably a d- or p-block metal, oxide, fluoride or oxyfluoride thereof, and more preferably is chromium, aluminium, or a Group VIIIa metal.

We have found that difluoromethane may be produced in step (b) with very high selectivity where the catalyst employed is a metal selected from the group consisting of nickel, aluminium, iron or chromium and in particular where the catalyst is an alloy or mixture of at least one of these metals. The alloy or mixture may also comprise other metals, for example molybdenum, copper or cobalt. Examples of preferred alloys include Hastelloy and stainless steel; stainless steel is an especially preferred alloy.

Furthermore we prefer that the catalyst is air treated prior to use, that is the catalyst is heated to elevated temperature in the presence of air, for example a temperature in the range from 300° C. to 500° C. Alternatively or additionally this catalyst pre-treatment may be carried out in the presence of hydrogen fluoride.

Further preferred catalysts are chromia and iron oxide, which although they may not promote as high a degree of selectivity to difluoromethane as the preferred alloys, are very robust catalysts. Chromia and iron oxide may also be given a pre-treatment prior to their use.

The catalyst may also comprise mixtures of metals, oxides, fluorides or oxyfluorides thereof, such as for example impregnated metal oxide or oxyfluorides, or simple mixtures. Thus, for example the catalyst may comprise chromia impregnated with iron, nickel, copper or other metals or compounds thereof, for example oxides or halides thereof or the catalyst may comprise a mixture of chromia and other metal oxides, for example iron oxide.

Other catalysts may also be used which lead to the production of monofluoromethane with a high degree of selectivity, for example a catalyst comprising zinc impregnated chromia or tin fluoride.

The catalyst may be supported or unsupported.

Accordingly in a further preferred embodiment of the invention, step (b) comprises heating bis(fluoromethyl)ether in the vapour phase at elevated temperature in the presence of a catalyst and optionally also in the presence of hydrogen fluoride. The catalyst is preferably at least one metal, metal oxide, metal fluoride or metal oxyfluoride.

According to a still further preferred embodiment of the invention, step (b) comprises heating bis(fluoromethyl)ether in the vapour phase at elevated temperature in the presence of a catalyst comprising a metal selected from the group consisting of nickel, chromium, aluminium and iron or an alloy of at least one of these metals or an oxide, fluoride or oxyfluoride thereof.

The temperature to which the bis(fluoromethyl)ether is heated in step (b) is dependant at least to some extent on whether the heating is effected in the presence of a catalyst. Where the heating is effected in the presence of a catalyst the preferred temperature is dependent on the particular catalyst used; generally where a catalyst is present the temperature need not be as high as when a catalyst is not present.

Typically the temperature need be no higher than about 450° C. where a catalyst is used in the presence of hydrogen fluoride. Thus, for example, where the heating is effected in the presence of stainless steel and hydrogen fluoride, the temperature is preferably at least about 250° C. and more preferably at least 300° C. but need be no higher than about 400° C., generally no higher than about 350° C. However, where the catalyst is chromia in the presence of hydrogen fluoride, the temperature is preferably from about 180° C. to about 320° C., more preferably from about 200° C. to about 280° C.

Step (b) of the process is conveniently carried out at about ambient pressure although superatmospheric or subatmospheric pressures may be used if desired. Indeed superatmospheric pressures up to about 15 bar at lower temperatures may be generally preferred since the yield of and selectivity to difluoromethane may be increased under such conditions.

After completion of step (b), the difluoromethane may be isolated from unchanged starting materials and by-products using conventional procedures, for example distillation.

BRIEF DESCRIPTION OF THE DRAWINGS

The invention will now be illustrated with reference to FIGS. 1 and 2 of the drawings in which.

Figure 1:
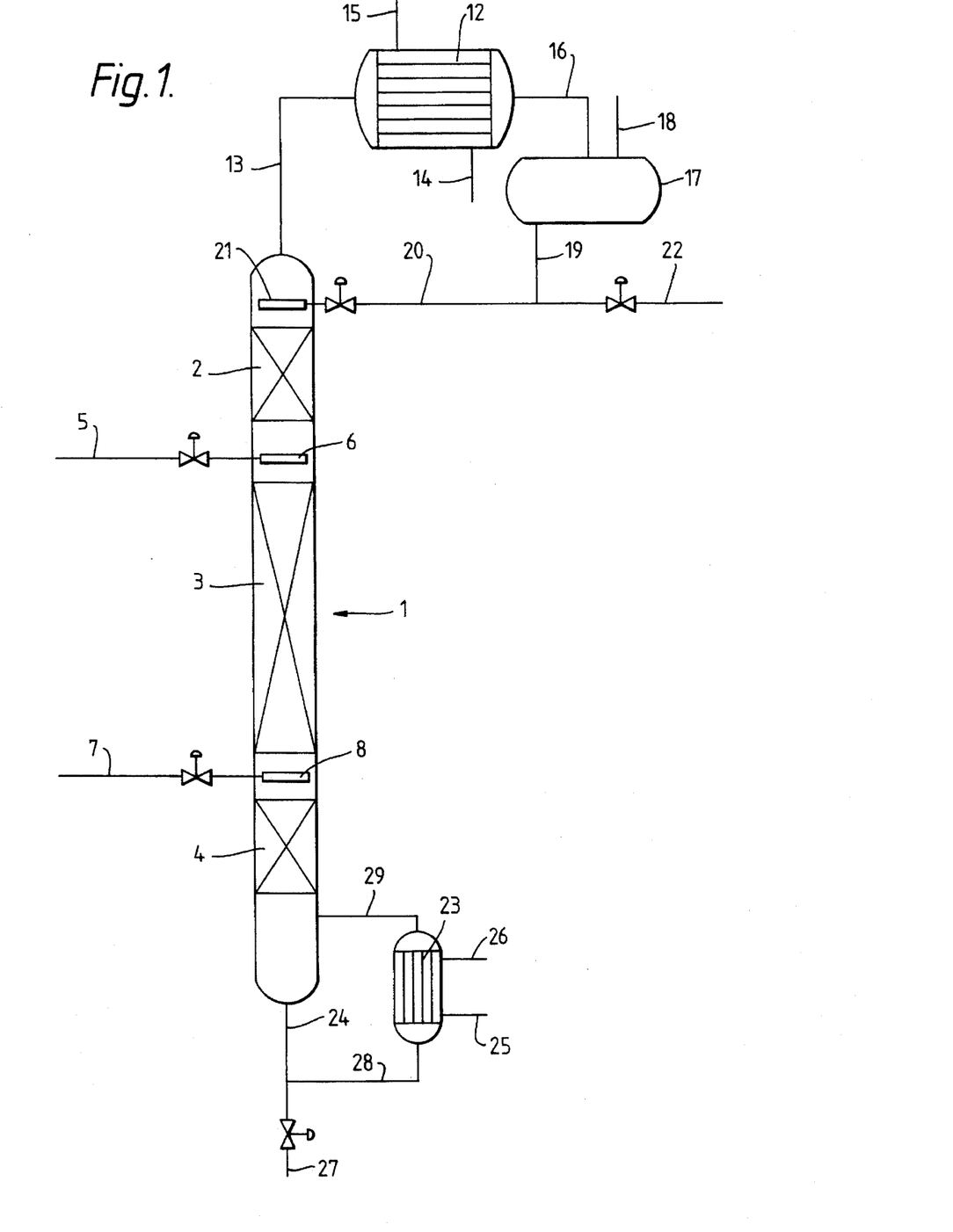
FIG. 1 is a schematic diagram showing a reaction/distillation column for use in a continuous process according to the invention.

In FIG. 1, the column 1, which may be constructed, for example, from Hastelloy alloy, comprises three sections, 2, 3, 4 of ordered Hastelloy corrugated packing. Section 2 represents the rectifying section of the column, section 3 represents the reaction section of the column and section 4 represents the stripping section of the column.

The column 1 is provided with an inlet for a formaldehyde feed stream 5 which is provided to the column through a distributor 6 positioned between the reaction section 3 and rectifying section 2. The column is also provided with an inlet for a hydrogen fluoride stream 7 which is provided to the column through a distributor 8 positioned between the reaction section 3 and the stripping section 4.

A condenser 12 is connected to the top of the column by line 13 and is provided with condensing medium inlet and outlet lines 14 and 15 respectively. A condensate line 16 connects the exit from the condenser to a reflux drum 17 provided with a vent 18 and exit line 19 which leads to a reflux return feed line 20 through which reflux product is returned to the top of the column via a reflux distributor 21, and an overhead product stream take-off line 22.

A reboiler 23 is connected to the bottom of the column via line 24 and is provided with reboiling medium inlet and outlet lines 25 and 26 respectively. Bottoms product is collected from the bottom of the column through product line 27 and bottoms product is fed to the reboiler by line 28 and then returned to the column by reboil return line 29.

In operation of the column, formaldehyde and hydrogen fluoride are fed to the column through feed lines 5 and 7, and distributors 6 and 8, respectively. A condensing medium, for example water or ethylene glycol, is circulated around the condenser 12, and a reboiling medium, for example steam or hot oil, is circulated around the reboiler 23.

Formaldehyde descends through the reaction section 3 of the column, reacting at each stage with hydrogen fluoride which rises through the reaction section. Bis(fluoromethyl)ether and excess hydrogen fluoride are flashed out at each stage and rise through the column. Water and hydrogen fluoride/water azeotrope descend through the column.

In the rectifying section 2 of the column, bis(fluoromethyl)ether and hydrogen fluoride are separated from water, formaldehyde and water/hydrogen fluoride azeotrope. The overhead product stream is withdrawn through line 13 and fed to the condenser 12 and from the condenser to the reflux drum 17 through condensate line 16. A reflux stream is returned to the column through line 20 and a product stream taken off through line 22.

In the stripping section 4, water and hydrogen fluoride/water azeotrope are separated from bis(fluoromethyl)ether and hydrogen fluoride and bottoms product is withdrawn from the base of the column through line 24. A bottoms product stream is taken off through line 27, and a reboil stream is fed through line 28 to a reboiler and then returned to the column through line 29.

Figure 2:
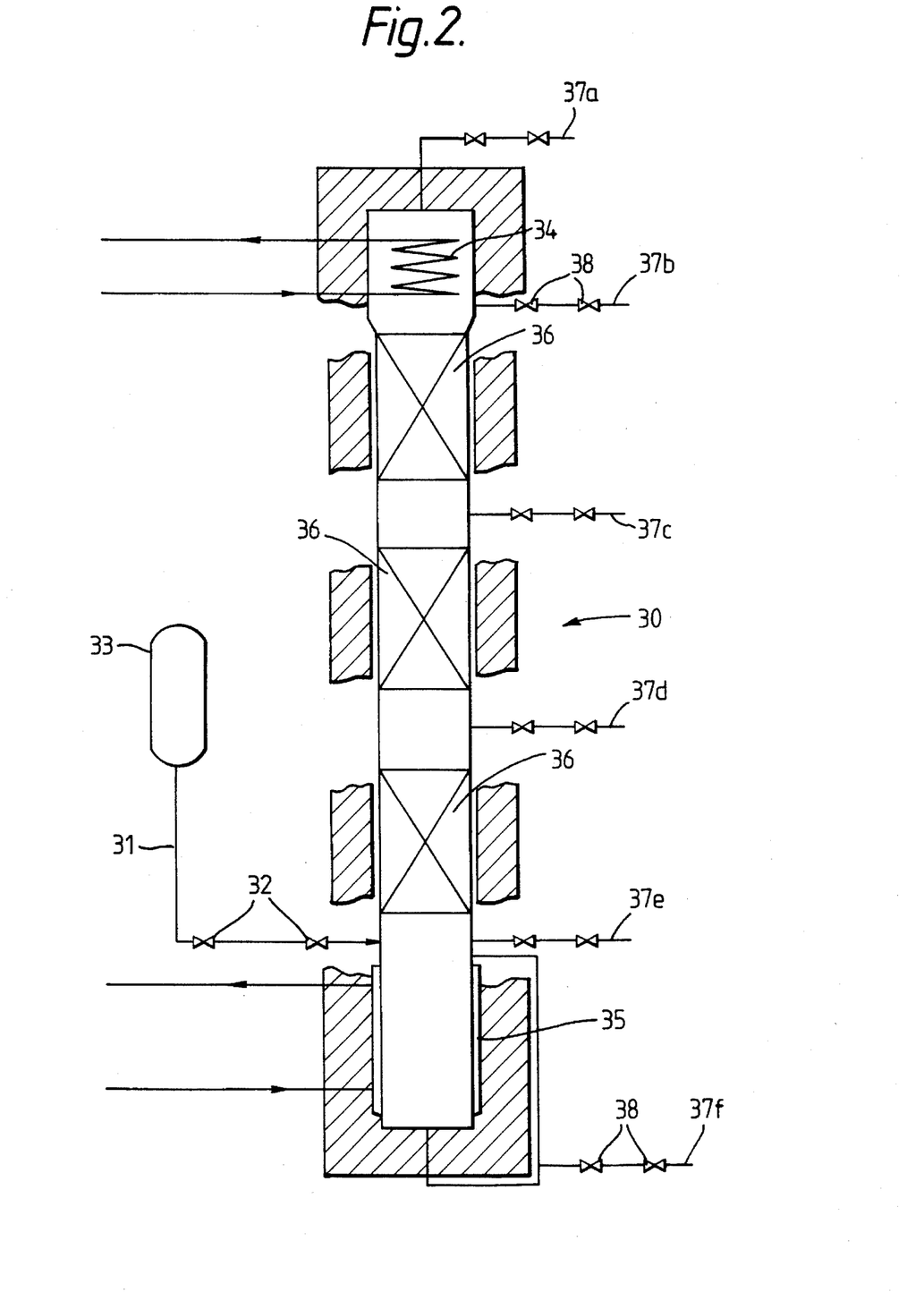
FIG. 2 is a schematic diagram of a vapour-liquid equilibrium column.

In FIG. 2, a batch operation vapour-liquid equilibrium column 30, constructed from polytetrafluoroethylene lined carbon steel is provided with a feed line 31 and valves 32 connecting a filling vessel 33 to the bottom of the column, a condensor 34 and a reboiler 35. The column is provided with sections of structured Hastelloy Sulzer BX packing 36, each section comprising a depth of packing of 6 inches. Each section of packing is separated from an adjacent section of packing by a perforated plate liquid re-distributor (not shown). Sampling lines 37 and associated valves 38 are provided from the column for the withdrawal of samples.

In operation of the column, a composition is charged to the column and all inlets/outlets to the column are closed. A hot oil stream is circulated through the re-boiler and a glycol stream is circulated through the condensor. The composition within the column is allowed to reach equilibrium. Samples are then withdrawn from the sampling points and analysed in order to determine the compositions at different heights within the column.

The invention is further illustrated by the following examples.

EXAMPLE 1.

SINGLE STAGE BATCH DISTILLATION 182.6 g of anhydrous hydrogen fluoride and 40.9 g of paraformaldehyde prills were charged to a closed 500 ml FEP pot provided with a polytetrafluoroethylene dip pipe for withdrawal of liquid samples and a polytetrafluoroethylene vapour outlet pipe for the withdrawal of vapour which is collected in a 100 ml FEP bottle containing alternately pyridine or water. The 500 ml pot was placed in a hot oil bath provided with temperature control.

Liquid and vapour samples were withdrawn at intervals of time and the composition of the samples was analysed in the following manner.

Vapour samples collected in pyridine were analysed for their bis(fluoromethyl)ether content by gas chromatography. Vapour samples collected in water were analysed for their hydrogen fluoride content by titration with sodium hydroxide, and for their formaldehyde content by titration with sodium bisulphite.

Liquid samples were injected into water or pyridine and analysed in the same way.

The composition of the residue remaining in the FEP pot at the end of the distillation was also analysed.

Figure 3:
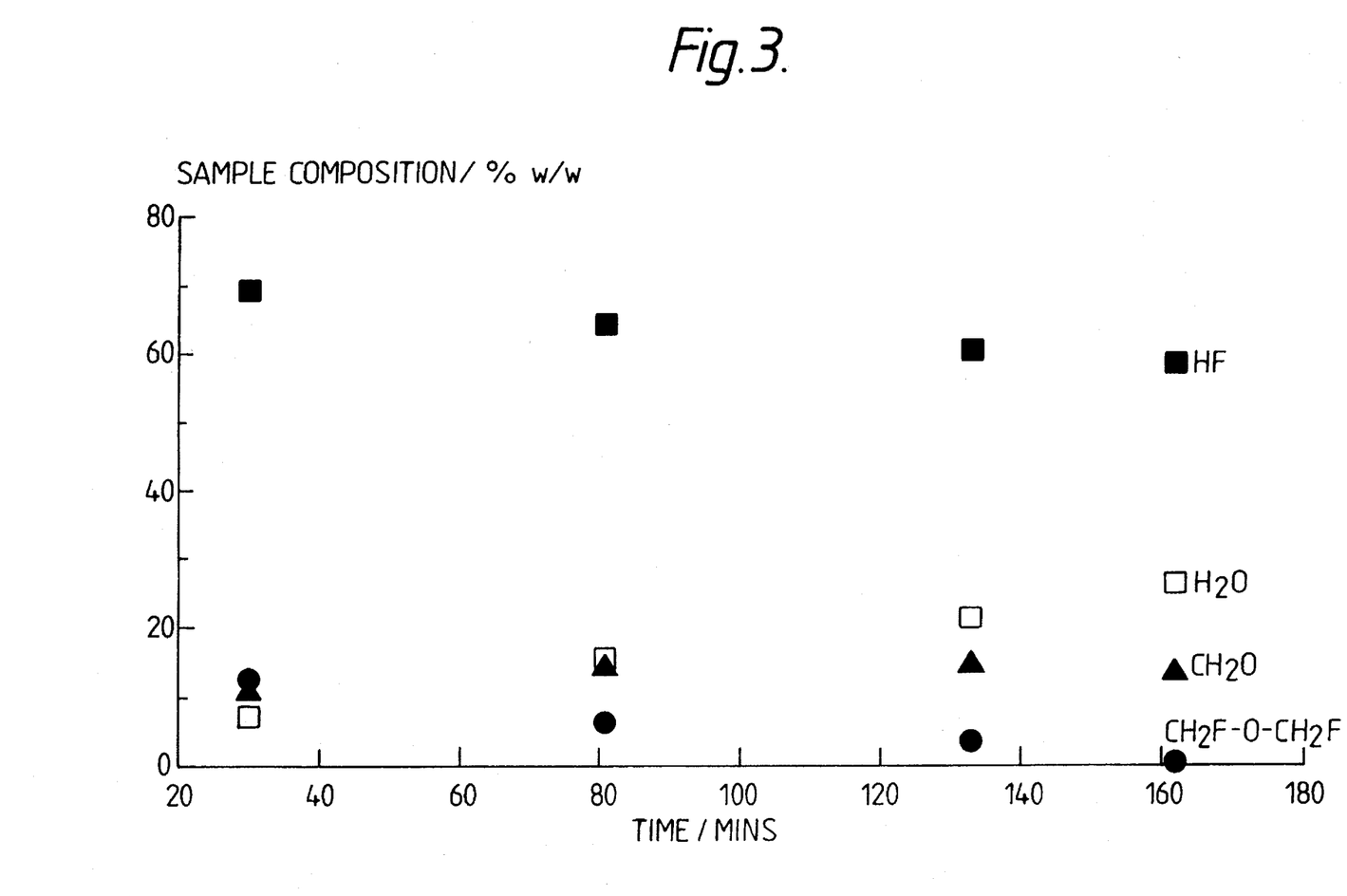
FIGS. 3 and 4 show the results of the Example in graphic form.
Figure 4:
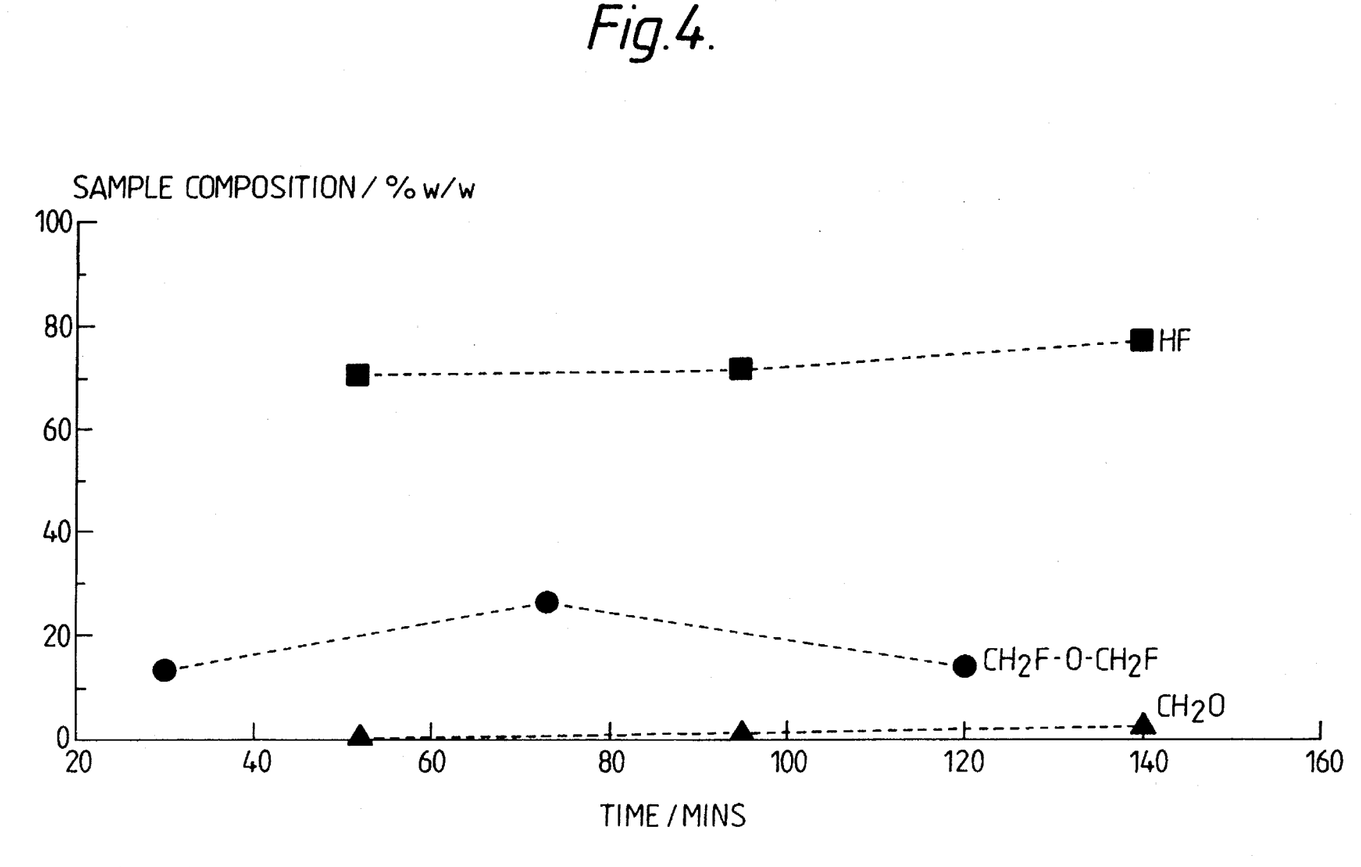

The results are shown in Table 1 below and in graphic form in FIGS. 3 and 4.

TABLE 1.

| (a) Vapour Samples collected in pyridine. | | |
|---|---|---|
| Time/mins | Temperature/°C. | $CH_2F$—O—$CH_2F$/% w/w |
| 30 | 31 | 12 |
| 73 | 35 | 27 |
| 120 | 42 | 13 |

| (b) Vapour Samples collected in water. | | | |
|---|---|---|---|
| Time/(mins) | Temperature/(°C.) | HF/(% w/w) | $CH_2O$/(% w/w) |
| 52 | 32 | 75 | 0 |
| 95 | 38 | 76 | 0.5 |
| 140 | 48 | 78 | 1.0 |

| (c) Liquid Sample Analysis. | | | | | |
|---|---|---|---|---|---|
| Time (mins) | Temperature (°C.) | $CH_2FOCH_2F$ (% w/w) | HF (% w/w) | $CH_2O$ (% w/w) | $H_2O$ (% w/w) |
| 30 | 31 | 12.5 | 69.2 | 11.0 | 7.3 |
| 81 | 37 | 6.1 | 64.2 | 14.1 | 15.6 |
| 133 | 46 | 3.4 | 60.4 | 14.6 | 21.6 |
| 162 | 60 | 0.4 | 58.5 | 13.5 | 27.6 |

Mass balances for hydrogen fluoride and formaldehyde were also calculated by measuring the total amount of formaldehyde and hydrogen fluoride collected in the distillate and remaining in the residue. The conversion of formaldehyde was 79%. By way of comparison a conversion of 55% is achieved when formaldehyde and hydrogen fluoride are contacted in a reaction pot under the same conditions but without distillation.

The example shows the advantages of separation of $CH_2F$—O—$CH_2F$ from water and increased formaldehyde conversion obtained by effecting the reaction between formaldehyde and hydrogen fluoride in a vessel in which distillation is simultaneously effected. It will be readily understood that this example illustrates operation of the invention at each single distillation stage within a multi-stage distillation column.

The following example 2 was carried out in the batch operation multi-stage vapour-liquid equilibrium column shown generally in FIG. 2.

EXAMPLE 2

976 g of a composition having the mole fraction composition shown in Table 2 was charged to the column.

All inlets and outlets to the column were closed, a hot oil stream was fed to the re-boiler and glycol was fed to the condensor. The still was left for 12 hours to reach equilibrium and samples were then withdrawn from the column, and analysed using the techniques previously described. The results are shown in table 2 below, in which all component amounts are in mole fractions.

TABLE 2

| SAMPLE POINT | HF | $H_2O$ | $CH_2O$ | $CH_2F$—O—$CH_2F$ |
| --- | --- | --- | --- | --- |
| 1b. | 0.855 | 0.070 | 0.022 | 0.053 |
| 1c. | 0.785 | 0.136 | 0.062 | 0.017 |
| 1d. | 0.685 | 0.210 | 0.102 | 0.004 |
| 1e. | 0.375 | 0.613 | 0.012 | 0.001 |
| 1f. | 0.399 | 0.598 | 0.001 | 0.003 |
| CHARGE | 0.403 | 0.557 | 0.040 | 0.000 |

The following examples 3 to 6 illustrate step (b) of the further preferred embodiment of the invention.

EXAMPLE 3.

HEATING BFME IN THE PRESENCE OF HF-TREATED CHROMIA

Bis(fluoromethyl)ether was vaporised by bubbling nitrogen through liquid bis(fluoromethyl)ether at room temperature at a flow rate of 75 mls/minute. The vapour was fed to an Inconel tube (length 12 inches and diameter 1 inch) packed with 120 g of chromia pellets which had been pre-treated by heating the pellets to 350° C. for 4 hours in a stream of hydrogen fluoride having a flow rate of 150 ml/minute. The tube was heated from room temperature to elevated temperature and the composition of the reactor off gas was followed (Gas Chromatography) as a function of temperature and the results are shown in Table 3.

TABLE 3

| | % Yield | | BFME | Molar Ratio |
| --- | --- | --- | --- | --- |
| Temp/°C. | $CH_3F$ | $CH_2F_2$ | Conversion/% | $CH_2F_2/CH_3F$ |
| 185 | 29.11 | 43.79 | 74.38 | 1.5 |
| 224 | 32.34 | 62.54 | 95.71 | 1.93 |
| 246 | 35.40 | 63.77 | 99.97 | 1.8 |
| 256 | 35.22 | 62.21 | 100.0 | 1.77 |
| 292 | 35.66 | 57.45 | 98.09 | 1.61 |

TABLE 3-continued

| | % Yield | | BFME | Molar Ratio |
| --- | --- | --- | --- | --- |
| Temp/°C. | $CH_3F$ | $CH_2F_2$ | Conversion/% | $CH_2F_2/CH_3F$ |
| 320 | 35.88 | 54.57 | 97.62 | 1.52 |

EXAMPLE 4.

HEATING BFME IN THE PRESENCE OF NICKEL DOPED CHROMIA 100 g of chromia pellets were added to a saturated aqueous solution of nickel nitrate and the water was then removed by direct heating to 150° C., to give a 2.7% nickel impregnated chromia catalyst. 100 g of the catalyst was charged to an Inconel reactor (length 12 inches and diameter 1 inch) and heated in nitrogen at 300° C. for 28 hours and then pre-fluorinated by heating in hydrogen fluoride at 350° C. for 4 hours. Finally the catalyst was heated in nitrogen at 250° C. for 15 hours.

Bis(fluoromethyl)ether was vaporised by bubbling nitrogen through liquid bis(fluoromethyl)ether at room temperature at a flow rate of 75 mls/minute. The vapour was fed to the Inconel reactor. The tube was heated from room temperature to elevated temperature and the composition of the reactor off gas was followed (Gas Chromatography) as a function of temperature and the results are shown in Table 4.

TABLE 4

| | % Yield | | BFME | Molar Ratio |
| --- | --- | --- | --- | --- |
| Temp/°C. | $CH_3F$ | $CH_2F_2$ | Conversion/% | $CH_2F_2/CH_3F$ |
| 223 | 36.78 | 60.35 | 97.14 | 1.64 |
| 234 | 28.25 | 69.10 | 97.35 | 2.45 |
| 241 | 21.60 | 77.56 | 99.16 | 3.6 |
| 251 | 23.42 | 73.27 | 97.82 | 3.13 |
| 265 | 26.48 | 71.64 | 98.12 | 2.7 |
| 279 | 24.45 | 72.35 | 99.53 | 3.0 |

EXAMPLE 5.

HEATING BFME IN THE PRESENCE OF MIXED IRON OXIDE/CHROMIA 112.7 g of a catalyst comprising 9:1 by weight iron (III) oxide and chromia was charged to an Inconel reactor (length 12 inches and diameter 1 inch) and heated in hydrogen fluoride at 300° C. for 12 hours. The catalyst was then heated in nitrogen at 230° C. for 15 hours.

Bis(fluoromethyl)ether was vaporised by bubbling nitrogen through liquid bis(fluoromethyl)ether at room temperature at a flow rate of 75 mls/minute. The vapour was fed to the Inconel reactor. The tube was heated from room temperature to elevated temperature and the composition of the reactor off gas was followed (Gas Chromatography) as a function of temperature and the results are shown in Table 5.

TABLE 5

| Temp/°C. | % Yield | | BFME | Molar Ratio |
|---|---|---|---|---|
| | $CH_3F$ | $CH_2F_2$ | Conversion/% | $CH_2F_2/CH_3F$ |
| 223 | 23.34 | 73.52 | 99.15 | 3.15 |
| 235 | 19.33 | 68.41 | 87.75 | 3.54 |

EXAMPLE 6.

HEATING BFME IN THE PRESENCE OF PRE-FLUORINATED ALUMINIUM FLUORIDE 103.9 g of aluminium fluoride was charged to an Inconel reactor (length 12 inches and diameter 1 inch), heated in nitrogen at 300° C. for 4 hours and then heated in hydrogen fluoride at 300° C. for 12 hours. The catalyst was then heated in nitrogen at 240° C. for 16 hours.

Bis(fluoromethyl)ether was vaporised by bubbling nitrogen through liquid bis(fluoromethyl)ether at room temperature at a flow rate of 75 mls/minute. The vapour was fed to the Inconel reactor. The tube was heated from room temperature to elevated temperature and the composition of the reactor off gas was followed (Gas Chromatography) as a function of temperature and the results are shown in Table 6.

TABLE 6

| Temp/°C. | % Yield | | BFME | Molar Ratio |
|---|---|---|---|---|
| | $CH_3F$ | $CH_2F_2$ | Conversion/% | $CH_2F_2/CH_3F$ |
| 235 | 30.46 | 68.5 | 98.96 | 2.25 |

We claim:

1. A process for the production of bis(fluoromethyl)ether which comprises reacting formaldehyde with hydrogen fluoride in a single reaction/distillation column operated under conditions of temperature and pressure so as to simultaneously (i) produce said bis(fluoromethyl)ether and by-product water and (ii) separate a by-product liquid phase in which the mole ratio of bis(fluoromethyl)ether to water is less than 1 from a desired product vapour phase in which the mole ratio of bis(fluoromethyl)ether to water is greater than 1.

2. A process as claimed in claim i in which the molar ratio of formaldehyde to hydrogen fluoride is in the range from about 1:2 to about 1:10.

3. A process as claimed in claim 1 in which the formaldehyde and hydrogen fluoride are caused to flow in countercurrent in the column.

4. A process as claimed in claim 3 in which the formaldehyde and at least a part of the hydrogen fluoride are fed to the column through different inlets.

5. A process as claimed in claim 4 in which formaldehyde is fed to the distillation column at a position above that at which at least a part of the hydrogen fluoride is fed to the column.

6. A process as claimed in claim 1 in which the formaldehyde is fed to the column as a solution of formaldehyde in hydrogen fluoride.

7. A process for the production of difluoromethane which comprises the steps of (a) contacting formaldehyde with hydrogen fluoride in a reaction distillation column as defined in claim 1 and (b) feeding the bis(fluoromethyl)ether to a reaction zone whereby to convert the bis(fluoromethyl)ether to difluoromethane.

8. A process as claimed in claim 7 in which step (b) comprises heating the bis(fluoromethyl)ether to elevated temperature in the vapour phase, optionally in the presence of catalyst.

9. A process as claimed in claim 8 in which the catalyst comprises a metal selected from the group consisting of nickel, chromium, aluminum and iron or an alloy of at least one of these metals, or an oxide, fluoride or oxyfluoride thereof.

10. A process for the production of bis(fluoromethyl)ether which comprises reacting formaldehyde with hydrogen fluoride in a distillation column operated at a temperature in the reaction section of the column which at the particular pressure employed corresponds to a temperature of from about 50° C. to about 80° C. at atmospheric pressure, to produce bis(fluoromethyl)ether and water and withdrawing a vapor in which the mole ratio of bis(fluoromethyl)ether to water is greater than 1.

11. A process for the production of bis(fluoromethyl)ether which comprises reacting formaldehyde with hydrogen fluoride in a distillation column to produce bis(fluoromethyl)ether and water and withdrawing a vapor in which the mole ratio of bis(fluoromethyl)ether to water is greater than 1 and wherein the molar ratio of formaldehyde to hydrogen fluoride fed to the distillation column is in the range from about 1:0.5 to about 50:1.

12. A process for the production of bis(fluoromethyl)ether which comprises reacting formaldehyde with hydrogen fluoride in a distillation column operated with a reflux ratio in the range from about 0.1 to about 10, to produce bis(fluoromethyl)ether and water and withdrawing a vapor in which the mole ratio of bis(fluoromethyl)ether to water is greater than 1.

* * * * *

UNITED STATES PATENT AND TRADEMARK OFFICE
CERTIFICATE OF CORRECTION

PATENT NO.    :    5,506,364

DATED         :    April 9, 1996

INVENTOR(S)   :    MARTIN et al.

It is certified that error appears in the above-identified patent and that said Letters Patent is hereby corrected as shown below:

On the title page: Item        [*] Notice", change the date from "September 6, 2011" to --November 12, 2012--.

Signed and Sealed this

Twentieth Day of August, 1996

Attest:

BRUCE LEHMAN

*Attesting Officer*        *Commissioner of Patents and Trademarks*